United States Patent
Prasad

(10) Patent No.: US 6,303,787 B1
(45) Date of Patent: Oct. 16, 2001

(54) INTERMEDIATES AND AN IMPROVED PROCESS FOR THE PREPARATION OF OMEPRAZOLE EMPLOYING THE SAID INTERMEDIATES

(75) Inventor: Konakanchi Durga Prasad, Banjara Hills (IN)

(73) Assignee: Natco Pharma Limited, Banjara Hills (IN)

( * ) Notice: Subject to any disclaimer, the term of this patent is extended or adjusted under 35 U.S.C. 154(b) by 0 days.

(21) Appl. No.: 09/427,217

(22) Filed: Oct. 26, 1999

(30) Foreign Application Priority Data

May 27, 1998 (IN) .......................... 1129/MAS/98

(51) Int. Cl.[7] ..................... C07D 401/12; C07D 403/12; C07D 213/82
(52) U.S. Cl. .................. 546/273.4; 546/304; 546/312
(58) Field of Search ........................... 546/273.4

(56) References Cited

U.S. PATENT DOCUMENTS

| | | | |
|---|---|---|---|
| 4,255,431 | 3/1981 | Junggren et al. ................... 514/338 |
| 5,578,732 | * 11/1996 | Kato et al. ........................ 546/273.7 |
| 5,958,955 | * 9/1999 | Gustavsson et al. ................ 514/339 |
| 6,147,103 | * 11/2000 | Anousis et al. ..................... 514/394 |
| 6,156,346 | * 12/2000 | Chen et al. ........................ 424/489 |
| 6,166,213 | * 12/2000 | Anousis et al. ................... 546/273.7 |

FOREIGN PATENT DOCUMENTS

| | | |
|---|---|---|
| 0005129 | 4/1979 | (EP) . |
| 0103553 | 6/1983 | (EP) . |
| 0484265 | 10/1991 | (EP) . |

* cited by examiner

*Primary Examiner*—Alan L. Rotman
(74) *Attorney, Agent, or Firm*—Merchant & Gould P.C.

(57) ABSTRACT

This invention relates to an improved process for the preparation of Omeprazole of the formula-I starting from 4-nitro-2,3,5-trimethylpyridine-N-oxide and through novel intermediates 2-hydroxymethyl-3,5-dimethyl-4-nitro pyridine of the formula II and novel 2-chloromethyl-3,5-dimethyl-4-nitro pyridine of the formula III. This invention also relates to processes for the preparation of the above said novel intermediates. Omeprazole is one of the world's widely used drugs for the treatment of ulcer diseases. This compound acts by irreversible inhibition of the $H^+ K^+$ ATPase enzyme, which is part of the proton pump located in the parietal cell of the stomach wall.

10 Claims, No Drawings

INTERMEDIATES AND AN IMPROVED PROCESS FOR THE PREPARATION OF OMEPRAZOLE EMPLOYING THE SAID INTERMEDIATES

FIELD OF INVENTION

The present invention, relates to process for the preparation of Omeprazole. This invention particularly relates to an alternate process for the preparation of Omeprazole of formula-I,

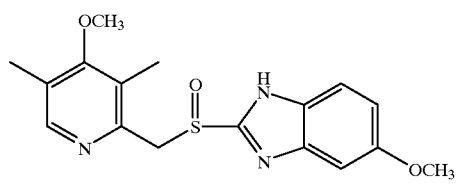

Formula-I using novel intermediates, 2-hydroxymethyl-3,5-dimethyl-4-nitropyridine of formula-II,

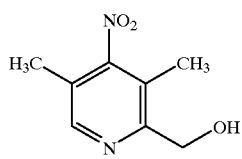

Formula-II and novel intermediate, 2-chloromethyl-3,5-dimethyl-4-nitro pyridine of formula-III.

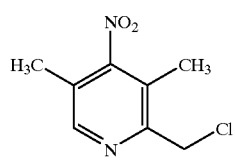

Formula-III

Omeprazole is one of the world's widely used drugs for the treatment of ulcer disease. This compound act by irreversible inhibition of the $H^+K^+$ATPase enzyme, which is part of the 'proton pump' located in the parietal cell of the stomach wall.

PRIOR ART

Omeprazole is first disclosed in Swedish patent 7804231 and the corresponding patents EP-0005129 A1 and U.S. Pat. No. 4,255,431.

2-(Lithium methyl sulphinyl)-5-methoxy-1H-benzimidazole of formula I-a where M is K, Na and Li is reacted with 2-chloro-3,5-dimethyl-4-methoxy pyridine of formula I-b, where z is a leaving group, to get Omeprazole of formula-I.

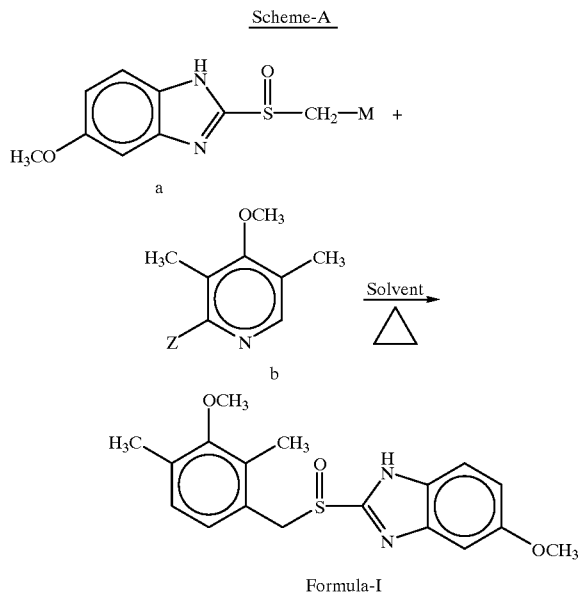

The following intermediates of formulae-c to m and IV, for the preparation of Omeprazole and the synthetic scheme for their improved processes have been disclosed in European patent-0103553 AI and are shown in schemes B and C.

Scheme-B
2, 3, 5-collidine of formula-c

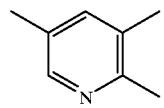

Formula-c is oxidized with acetic acid and hydrogen peroxide to get 2,3,5-collidine N-oxide of formula-d,

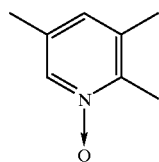

Formula-d which on treatment with nitrating mixture yields 4-nitro-2,3,5-trimethylpyridine-N-oxide of formula IV.

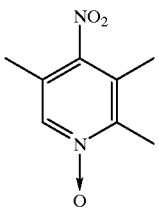

Formula-IV

The compound of formula-IV is treated with methanol and sodium hydroxide to get 4-methoxy-2,3,5-trimethylpyridine-N-oxide of formula-e,

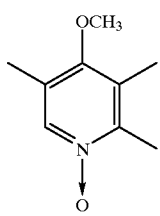
Formula-e which on treatment with acetic anhydride gives 2-acetyloxymethyl-3,5-dimethyl-4-methoxypyridine of formula-f,

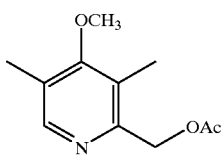
Formula-f which on hydrolysis gives 2-hydroxymethyl-3,5-dimethyl-4-methoxy pyridine of formula-g.

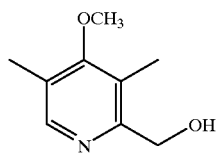
Formula-g

The compound of formula-g is reacted with thionyl chloride to get 2-chloromethyl-3,5-dimethyl-4-methoxypyridine hydrochloride of formula-h.

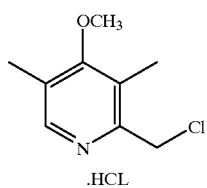
Formula-h

Scheme-C
3, 5-Lutidine of formula-i,

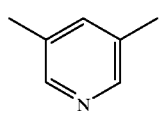
Formula-i is reacted with acetic acid and hydrogen peroxide to get 3,5-dimethylpyridine-N-oxide of formula-j.

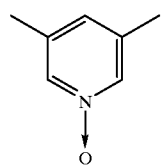
Formula-j which on reaction with nitrating mixture gives 4-nitro-3,5-dimethylpyridine-N-oxide of formula-k.

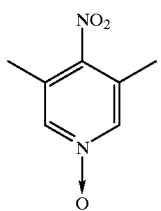
Formula-k

The compound of formula-k is reacted with sodium hydroxide and methanol to get 4-methoxy-3,5-dimethylpyridine-N-oxide of formula-l

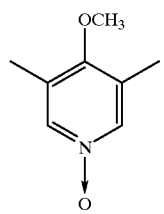
Formula-l

The compound of formula-l is reacted with dimethyl sulphate to get 3,5-dimethyl-1,4-dimethoxypyridinium methosulphate of formula-m,

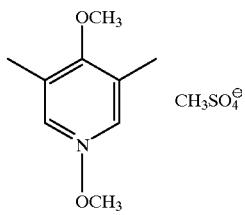
Formula-m which on treatment with methanol and ammonium persulphate yields the compound of formula-g.

The Spanish patent No 9002764/European Patent No.0484265 $A_1$ also discloses an alternate process for the preparation of Omeprazole (Schemes-D&E) and the intermediate 2-hydroxymethyl-3,5-dimethyl-4-nitro pyridine hydrochloride (Scheme-F).

Scheme-D
4-Nitro-2, 3, 5-trimethylpyridine -N-oxide of formula-IV,

Formula IV

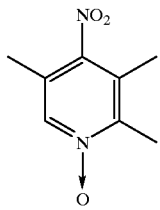

is reacted with phosphorous trichloride to get 4-nitro-2,3,5-trimethylpyridine of formula-V, Formula V

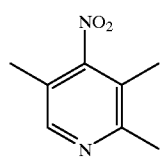

which on reaction with trichloro isocyanuric acid gives 2-chloromethyl-3,5-dimethyl-4-nitro pyridine hydrochloride of formula-VI Formula VI

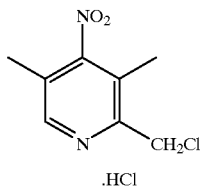

The compound of formula-VI is reacted with sodium hydroxide and methanol with 5-methoxy-2-mercapto benzimidazole of formula-VII, Formula VII

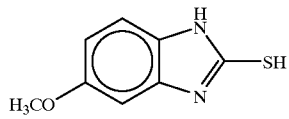

To get compound of formula VIII.

Formula VIII

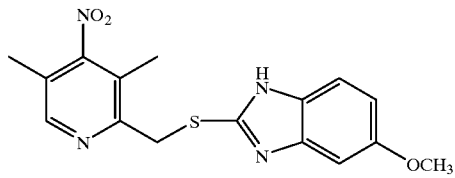

The compound of formula-VIII is reacted with sodium methoxide and benzyl triethyl ammonium chloride in methanol to get desoxyomeprazole of formula-IX.

Formula IX

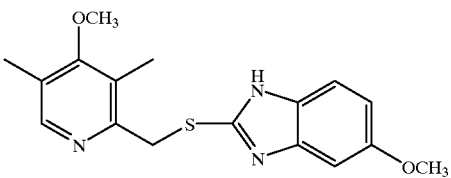

The compound of formula-IX (as 2-ethylhexanoic acid salt) is reacted with hydrogen peroxide in the presence of ammonium molybdate to get omeprazole of formula-I.

Scheme-E
4-nitro-2, 3, 5-trimethylpyridine-N-oxide of formula-IV is reacted with trichloroisocyanuric acid to get 2-chloromethyl-3, 5-dimethyl-4-nitropyridine-N-oxide of formula-X, Formula-X

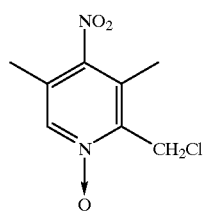

which on reaction with phosphorous trichloride to get 2-chloromethyl-3,5-dimethyl-4-nitro-pyridine hydrochloride of formula-VI.

Formula-VI

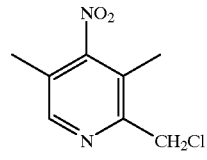

The compound of formula-VI is converted to Omeprazole of formula-I as mentioned in scheme-D.

Scheme-F
4-Nitro-2, 3, 5-trimethyl pyridine-N-Oxide of formula-IV is reacted with acetic anhydride in presence of 4-dimethylaminopyridine to get 2-acetyloxymethyl-3, 5-dimethyl-4-nitro-pyridine of formula-XI.

Formula-XI

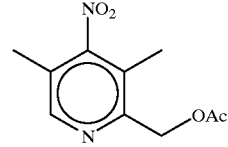

which on acid hydrolysis gives 2-hydroxymethyl-3,5-dimethyl-4-nitropyridine hydrochloride of formula-XII Formula-XII

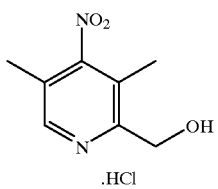
.HCl

Formula-XV

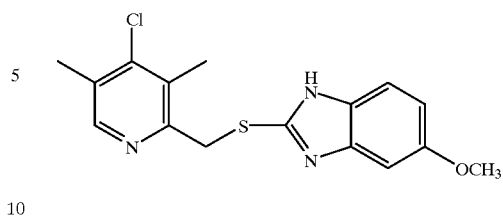

On our repeating the process disclosed in ES 9002764/EP 0484265A₁ for obtaining Omeprazole, we found that the Omeprazole obtained is contaminated with chlorine containing impurities at about 2% level. The cause for this impurity was traced to the instability of HCl salts of compounds of the formulae-VI and XII resulting in formation of 4-chloro derivatives by displacement of 4-nitro group of the formula by chloride ion.

In other words, the impurity 2-chloromethyl-4-chloro-3,5-dimethylpyridine of formula-XIII,

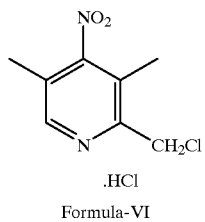
.HCl
Formula-VI

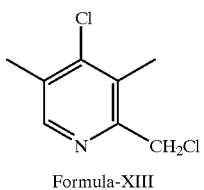
Formula-XIII originates from 2-chloromethyl-3,5-dimethyl-4-nitropyridine hydrochloride of formula-VI (as HCl), the impurity 2-hydroxymethyl-4-chloro-3,5-dimethyl pyridine of formula-XIV,

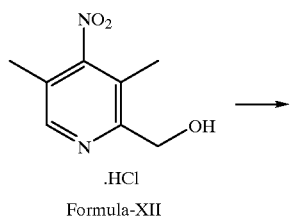
.HCl
Formula-XII

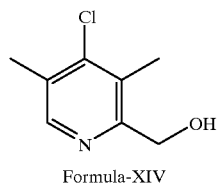
Formula-XIV originates from 2-hydroxymethyl-3,5-dimethyl-4-nitropyridine hydrochloride of formula-XII (as HCl salt)

In our sustained efforts to produce omeprazole minimizing the formation of impurities of the formula-XIII, formula-XIV and in the later stage the impurity 5-methoxy-2-(((4-chloro -3,5-dimethylpyridinyl)methyl)thio)-1H-benzimidazole of formula-XV, with limit less than 0.1%, we could develop a process based on our findings that the compound of formula-XI is hydrolyzed by base hydrolysis avoiding acid hydrolysis, and in the subsequent stage the compound 2-chloromethyl-3,5-dimethyl-4-nitropyridine of formula-III is isolated in base form by neutralizing immediately after completion of the reaction with a base. Such a procedure avoids the formation of impurities 2-hydroxymethyl-3,5-dimethyl-4-chloropyridine of formula-XIV, 2-chloromethyl-3,5-dimethyl-4-chloropyridine of formula-XIII and the impurity of formula-XV, Formula-XV

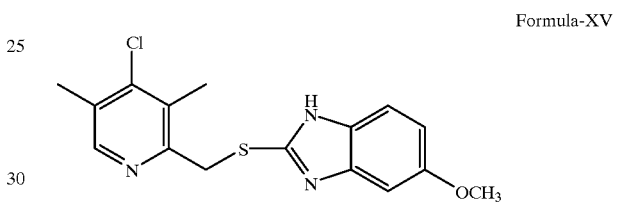

in the later stage.

2,3,5-trimethyl-4-nitropyridine-N-oxide, of formula-IV, can then be rearranged to 2-acetyloxymethyl-3,5-dimethyl-4-nitropyridine of the formula-XI, which on base hydrolysis gives 2-hydroxymethyl-3,5-dimethyl-4-nitropyridine, of the formula-II. This intermediate of formula-II is purified by re-crystallization from different solvents.

The compound, of the formula-II is reacted at a temperature in the range of 0–15° C. with a chlorinating agent, such as thionyl chloride to get 2-chloromethyl-3,5-dimethyl-4-nitro-pyridine hydrochloride of the formula-VI which is neutralized immediately to obtain compound of formula-III in base form with the impurity 2-chloromethyl-4-chloro-3,5-dimethylpyridine of formula-XIII in less than 0.2% level.

The 2-chloromethyl-3,5-dimethyl-4-nitropyridine of formula-III is dissolved in a protic solvent and reacted with 2-mercapto-5-methoxy benzimidazole of the formula-VII with a base to get 5-methoxy-2-(((3,5-dimethyl-4-nitro-2-pyridinyl)methyl)thio)-1H-benzimidazole of formula-VIII. After recrystallization from suitable solvents, pure compound-VIII is obtained with an impurity, 5-methoxy-2-(((3,5-dimethyl-4-chloro-2-pyridinyl)methyl)thio-1H-benzimidazole, of formula-XV less than 0.1%.

The compound of the formula-VIII is refluxed with methanolic sodium methoxide solution to obtain 5methoxy-2-(((3,5-dimethyl-4-methoxy-2-pyridinyl)methyl)thio)-1H-benzimidazole, of the formula-IX.

The desoxy omeprazole of the formula-IX is reacted with oxidizing agent in the presence of a protic solvent at low temperature i.e. −5 to 0° C. to get pharmacopeial grade Omeprazole. The Omeprazole thus prepared contains impurities 5-methoxy-2-(3,5-dimethyl-4-chloro-2-pyridinyl) methyl sulphinyl)-1H-benzimidazole of formula-XVI,

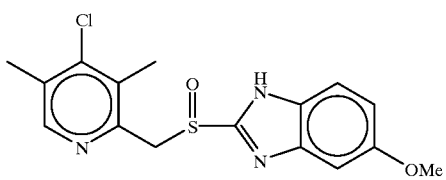

Formula-XVI and 5-methoxy-2-(3,5-dimethyl-4-chloro-2-pyridinyl) methylsulphonyl)-1H-benzimidazole of formula-XVII,

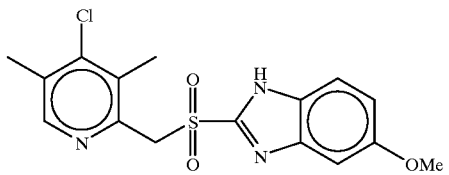

Formula-XVII at less than 0.1% level.

The present invention provides an alternate process for the preparation of omeprazole using novel intermediates 2-hydroxymethyl-3,5-dimethyl-4-nitro pyridine of formula-II and 2-chloro methyl-3,5-dimethyl-4-nitro pyridine of formula-III. These two intermediates are very stable when compared to its hydrochloride salts. These two compounds are reacted with para toluene sulphonic acid and to get para toluene sulphonate salts of formulae XVIII and XIX.

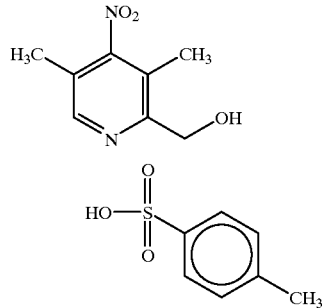

Formula-XVIII

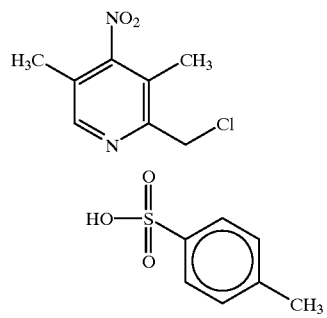

Formula-XIX

The 2-Hydroxymethyl-3,5-dimethyl-4-nitropyridine of formula-II and 2-chloro methyl-3,5-dimethyl-4-nitro pyridine of formula-III both in their base form, are prepared according to the process disclosed above. These compounds are very stable when compared to their hitherto known hydrochloride salts which are produced according to the process disclosed in the above Spanish patent. The employment of these now intermediates results in the reduction of impurities in the preparation of Omeprazole.

1. The present invention provides an improved process for the preparation of Omeprazole having impurities less than 0.1%
2. The present invention also provides an, alternative process for the preparation of Omeprazole starting from 2,3,5-trimethyl-4-nitro pyridine-N-oxide of formula-IV and through novel intermediate 2-hydroxymethyl-3,5-dimethyl-4-nitro pyridine of formula-II and 2-chloromethyl-3,5-dimethyl-4-nitro pyridine of formula-III.
3. The present invention also provides novel intermediates 2-hydroxymethyl-3,5-dimethyl-4-nitro pyridine of formula-II and 2-chloromethyl-3,5-dimethyl-4-nitro pyridine of formula-III and processes for their preparation.

The Scheme of the Present Invention

This invention, particularly relates to an alternate process for the preparation of Omeprazole useful as anti-ulcer drug having the formula-I through intermediate desoxy-Omeprazole of formula-IX.

The compound of formula-IX is prepared through intermediate 5-methoxy-2-(((3,5-dimethyl-4-nitro-2-pyridinyl) methyl)thio)-1-H-benzimidazole of Formula-VIII. The compound of formula-VIII is prepared through intermediate 2-chloromethyl-3,5-dimethyl-4-nitropyridine of Formula-III, by coupling in alkali medium with 5-methoxy-2-mercapto benzimidazole of formula-VII.

The compound of formula-III is prepared through novel intermediate 2-Hydroxymethyl-3,5-dimethyl-4-nitropyridine of formula-II.

The compound of formula-II is prepared through intermediate 2-acetyloxymethyl-3,5-dimethyl-4-nitropyridine of formula-XI, which is synthesized from 4-nitro-2,3,5-trimethyl pyridine-N-oxide of formula-IV.

Accordingly, the present invention provides an alternate process for the preparation of Omeprazole which comprises:
i) Rearranging 4-nitro-2,3,5-trimethylpyridine-N-oxide of the formula-IV, by conventional methods to 2-acetyloxymethyl-3,5-dimethyl-4-nitropyridine of the formula-XI.
ii) Hydrolyzing the compound of the formula-XI to 2-hydroxymethyl-3,5-dimethyl-4-nitropyridine of the formula-II by employing a base.
iii) Chlorinating the compound of the formula-II with a chlorinating agent at a temperature in the range of 0–15° C. to obtain 2-chloromethyl-3,5-dimethyl-4-nitropyridine of the formula-III.
iv) Coupling of the compound of the formula-III with 5-methoxy-2-mercapto benzimidazole of the formula-VII in aqueous alkali to obtain 5-methoxy 2-(((3,5-dimethyl-4nitro-2-pyridinyl)methyl)thio)-1H-benzimidazole of the formula-VIII.
v) Converting the compound of the formula-VIII with a protic solvent to obtain 5-methoxy-2-(((3,5-dimethyl-4-methoxy-2-pyridinyl)methyl)thio)-1H-benzimidazole of formula-IX and
vi) Oxidizing the compound of the formula-IX with an oxidising agent to obtain omeprazole [5-methoxy-2-(((3,5-dimethyl-4-methoxy-2-pyrdinyl)methyl) sulphinyl)-1H-benzimidazole] of the formula-I as given above.

Accordingly to another feature of the present invention is to provide a process for the preparation of novel 2-hydroxymethyl-3,5-dimethyl-4-nitropyridine of the formula-II which comprises:
i. Rearranging 4-nitro-2,3,5-trimethylpyridine-N-oxide of the formula-IV, by conventional methods to 2-acetyloxy-3,5-dimethyl-4-nitropyridine of the formula-XI.

ii. Hydrolyzing the compound of the formula-XI to 2-hydroxymethyl-3,5-dimethyl-4-nitropyridine of the formula-II by employing a base.

Accordingly, yet another feature of the present invention is provided a process for the preparation of novel 2-chloromethyl-3,5-dimethyl-4-nitropyridine of the formula-III which comprises:

i. Rearranging 4-nitro-2,3,5-trimethylpyridine-N-oxide of the formula-IV, by conventional methods to 2-acetyloxymethyl-3,5-dimethyl-4-nitropyridine of the formula-XI.

ii. Hydrolyzing the compound of the formula-XI to 2-hydroxymethyl-3,5-dimethyl-4-nitropyridine of the formula-II by employing a base.

iii. Chlorinating the compound of the formula-II with a chlorinating agent at a temperature in the range of 0–15° C. to obtain 2-chloromethyl-3,5-dimethyl-4-nitropyridine of the formula-III.

The present invention also includes the novel intermediates 2-hydroxymethyl-3,5-dimethyl-4-nitropyridine of the formula-II and 2-chloromethyl-3,5-dimethyl-4-nitropyridine of the formula-III.

In a preferred embodiment of the present invention, the rearrangement in step (i) may be effected by employing acetic anhydride at a temperature in the range 70 to 90° C. The base used in step (ii) may be selected from sodium hydroxide, potassium hydroxide. The chlorinating agent employed in step (iii) may be selected from thionylchloride, phosphorous oxychloride and phosphorous pentachloride. The alkali used in step (iv) may be sodium hydroxide and potassium hydroxide. This reaction is conducted in the presence of a protic solvent such as methanol and ethanol.

The step (v) of the process of the present invention may be carried out employing sodium methoxide in the presence of methanol. The oxidizing agent in step (vi) may be selected from metachloro perbenzoic acid, hydrogen peroxide in combination with a catalyst such as ammonium molybdate, vanadium pentoxide etc. Preferable oxidizing agent is urea-hydrogen peroxide complex (C. Lu et al., J.Am.Chem.Soc. 1941,63,1507). This oxidizing agent has not so far been employed in this step which accordingly adds further novelty to the invention.

The invention is described in detail in the example given below which is provided by way of illustration only and therefore should not be construed to limit the scope of the present invention.

EXAMPLE-I a) Preparation of 2-Hydroxymethyl-3,5-dimethyl-4-nitropyridine of formula-II (base)

151.3 gms (1.4833 mole) of acetic anhydride was added at 45–50° C. to a mixture of 90.0 gm (o.4595 moles) of 4-nitro-2,3,5-trimethylpyridine-N-oxide of formula-IV and 45.0 gms of acetic acid and heated to 85° C. and maintained at the temperature at 85–90° C. for 4 hrs. 75 ml of methanol was added to the reaction mixture at room temperature and distilled off acetic acid and methanol at temperature of 60–65° C. under vacuum to get an oil. 40% Sodium hydroxide solution (240 g) was added to the cooled oil at 0–5°°C. and stirred for 4 hrs. The crude product was obtained by extraction of the reaction mass with methylene chloride and distillation of the solvent. Pure 2-hydroxymethyl-3,5-dimethyl-4-nitropyridine of formula-II was obtained by re-crystallization of the crude material in toluene.

Yield—60.0 gms (60.0%)
Purity—99.5% (by HPLC)
MR—65.5° C.
Mass, NMR & IR spectra attached
p—Toluene sulphonic acid salt =M.R.–149° C.

b) Preparation of 2-Chloromethyl-3,5-dimethyl-4-nitropyridine of formula-III (base)

8.0 ml (0.11 mole) of thionyl chloride in 20.0 ml of methylenechloride was added to a solution of 20.0 gms 2-hydroxymethyl-3,5dimethyl-4-nitropyridine, of formula-II obtained in step-(a), at temperature of 10–15° C. over a period of 1 hr. The reaction is maintained at 10–15° C. for further 30 min. Aqueous 10% solution of sodium carbonate was slowly added to the reaction mixture at 10–15° C. and pH adjusted to 8.0 to 8.5. The organic base (compound) is over anhydrous sodium sulfate and solvent was removed under vacuum to obtain crude product. (purity 85%) Pure compound is isolated by re-crystallization from acetonitrile.

HPLC purity=99.8% MR–55.4° C.
Mass, NMR & IR spectra attached
p-Toluene sulphonic acid salt=M.R.–174.4° C.

c) Preparation of 5-Methoxy-2-(((3,5-dimethyl4-nitro-2-pyridinyl)methyl)thio)-1H-benzimidazole of formula-VIII A solution of 10.0 gms (0.25 mole,) of sodium hydroxide in 50 ml of water is slowly added to a suspension of 21.54 gms (0.1197 mole) of 2-mercapto-5-methoxy benzimidazole of formula-VII in 48.0 ml of methanol under N2 atmosphere at 10–15° C. Then a solution of 28.2 gms (85% pure) (0.1197 mole) of 2-chloromethyl-3,5-dimethyl-4-nitropyridine of formula-III as it is obtained in step-b in 84.0 ml of the methanol is added at 10–15° C. After stirring at 10–15° C. for 30 min, 250 ml of water is added and the mixture is again stirred for 30 min. Solid product is filtered and washed with 5% sodium hydroxide solution to remove unreacted 5-methoxy-2-mercapto benzimidazole of formula-VII. Recystallisation from dimethylformamide and acetonitrile gave pure product.

Yield 31.0 gms (75%)
MR—126–128° C.
HPLC Purity: 99.8%.

d) Preparation of 5-Methoxy-2-(((3,5-dimethyl-4-methoxy-2-pyridinyl)methyl)thio)-1H-benzimidazole. monohydrate of the formula-IX The traces of water present in 83.0 gms (0.241 moles) of 5-methoxy-2-(((3,5-dimethyl -4-nitro-2-pyridinyl)methyl) thio)-1H-benzimidazole of formula-VIII obtained in step-c were separated by azeotrope distillation in 400 ml of benzene, and benzene was distilled off completely and the residual solid was dissolved in 100 ml of methanol. At reflux temperature 253.0 ml (1.204 moles) of sodium methoxide solution was added over a period of 2 hrs. Later 100 ml of methanol was distilled. The mass was maintained at reflux temperature for 6 hrs. Checked TLC for absence of starting material. The pH was adjusted to 8–8.5 with acetic acid and the inorganics were filtered. Distilled off methanol under vacuum, extracted the product into methylene chloride (500 ml) washed with 5% NaOH (100 ml) and then with water (100 ml). The methylene chloride layer was given activated carbon (5.0 gms) treatment, filtered and dried over anhydrous sodium sulphate. The solvent was removed by distillation and the residual gum was dissolved in 100 ml of methanol, treated with 200 ml of water and stirred at room temperature till solid was formed. The solid was filtered and washed with DM water (50.0 ml), dried at 40–50° C. under vacuum, to obtain the compound of formula-IX as monohydrate.

HPLC Purity=99.5%.

MC=5–8%

Yield: 68.0 gms (80%)

e) Preparation of 5-Methoxy-2-(((3,5-dimethyl-4-methoxy-2-pyridinyl)methyl) sulphinyl)-1H-benzimidazole(Omeprazole) of formula-I 50.0 gms (0.144 moles) of 5-methoxy-2-(((3,5-dimethyl-4-methoxy-2-pyridyl)methyl)thio)-1H benzimidazole monohydrate, of formula-IX obtained in step-d was dissolved in 400.0 ml of methanol, cooled to +5° C. The pH of the solution was adjusted to 8.5 with sodium carbonate solution (25%), treated with urea-hydrogen peroxide complex. 33.0 gms (0.288 mol) and stirred to dissolve at 5–10° C., added acetic anhydride (18.0 gms-0.1765 moles) slowly at 5–10° C. and maintained the pH of the reaction mixture at 8–8.5 by simultaneous addition of 25% sodium carbonate solution. Then the reaction mass was maintained at 5–10° C. for 30 min. Checked the TLC till starting material was absent. Added 700 ml of water and stirred for 30 min at 0–5° C. The compound was extracted with 4×200 ml of methylene chloride. The combined methylene chloride layer again extracted with 200 ml of 3% sodium hydroxide solution, given activated carbon treatment (5.0 gms) for sodium hydroxide solution. Filtered, filtrate cooled to 0° C. and neutralized with 1.5% acetic acid solution to pH 7.5–8.0 at 0–5° C. The precipitate was filtered and washed with acetone (50 ml). The product was dried at 40–45° C. under vacuum to obtain Omeprazole.

The Omeprazole prepared confirms to pharmaceutical standards.

Yield—42.0 gms (85.00%)

What is claimed is:

1. A process for the preparation of 5-methoxy-2-(((3,5-dimethyl-4-methoxy-2-pyridinyl)methyl)sulphinyl)-1H-benzimidazole (Omeprazole) of formula I, which comprises:

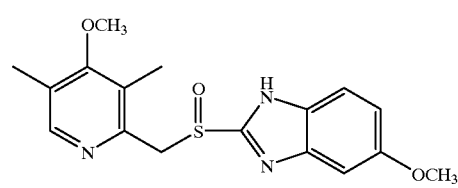

Formula-I i) Rearranging 4-nitro-2,3,5-trimethyl pyridine-N-oxide of the formula-IV to 2-acetyloxymethyl-3,5-dimethyl-4-nitropyridine of Formula XI by employing acetic anhydride;
ii) Hydrolyzing the compound of formula-XI to 2-hydroxymethyl-3,5-dimethyl-4-nitropyridine of formula-II by employing a base;
iii) Substituting the hydroxy group of the compound of formula-II with a chloride ion through the use of a chlorinating agent at a temperature in the range of 0–15° C. and neutralization with a base to obtain 2-chloromethyl-3,5-dimethyl-4-nitropyridine of formula III;
iv) Coupling the compound of formula-III with 5-methoxy-2-mercapto benzimidazole, of formula VII in aqueous alkali to obtain 5-methoxy-2(((3,5-dimethyl-4-nitro-2-pyridinyl)methyl)thio)-1H-benzimidazole of formula-VIII;
v) Converting the compound of formula-VIII by reflux with sodium methoxide solution to obtain 5-methoxy-2-(((3,5-dimethyl-4-methoxy-2-pyridinyl)methyl)thio)-1H-benzimidazole of formula-IX and
vi) Oxidizing the compound of formula-IX with an oxidizing agent at a temperature in the range of 5–10° C. to obtain 5-methoxy-2-(((3,5-dimethyl-4-methoxy-2-pyridinyl)methyl)sulphinyl)1H-benzimidazole (Omeprazole) of formula I.

2. A process for the preparation of 2-Hydroxymethyl-3,5-dimethyl-4-nitropyridine of formula-II which comprises:

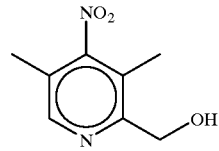

Formula-II i) Rearranging 4-nitro-2,3,5-trimethyl pyridine-N-oxide of formula-IV to 2-acetyloxymethyl-3,5-dimethyl-4-nitropyridine of Formula XI and
ii) Hydrolyzing the compound of formula-XI to 2-hydroxymethyl-3,5-dimethyl-4-Nitro pyridine of formula II by employing a base.

3. A process for the preparation of 2-chloromethyl-3,5-dimethyl-4-nitropyridine, of formula-III which comprises:

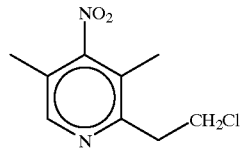

Formula-III i) Rearranging 4-nitro-2,3,5-trimethyl pyridine-N-oxide of the formula-IV to 2-acetyloxymethyl-3,5-dimethyl4-nitropyridine of Formula XI;
ii) Hydrolyzing the compound of formula-XI to 2-hydroxymethyl-3,5-dimethyl-4-nitropyridine of formula-II by employing a base and
iii) Chlorinating the compound of the formula-II with a chlorinating agent at a temperature in the range of 0–15° C. to obtain 2-chloromethyl-3,5-dimethyl-4-nitropyridine of the formula-III.

4. A process as claimed in one of claims 1 to 3 wherein the rearrangement in step-(i) is effected by employing acetic anhydride at a temperature in the range of 70–90° C.

5. A process according to claim 1, wherein the the base employed in step-(ii) is selected from sodium hydroxide and potassium hydroxide.

6. A process according to claim 1, wherein the chlorinating agent employed in step-(iii) is selected from thionyl chloride, phosphorous oxy chloride and phosphorous pentachloride.

7. A process as claimed in claim 1 wherein the alkali used in step-(iv) is selected from sodium hydroxide and potassium hydroxide and the reaction is conducted in the presence of a protic solvent.

8. A process according to claim 1, wherein the oxidizing agent in step-(vi) is selected from meta chloro perbenzoic acid and hydrogen peroxide in combination with a catalyst selected from ammonium molybdate and vanadium pentoxide.

9. A process according to claim 1, wherein the oxidizing agent used is urea hydrogen peroxide complex.

10. A process according to claim 1, wherein the base used in step-(iii) is selected from sodium carbonate and potassium carbonate.

* * * * *